United States Patent [19]
Bremer et al.

[11] Patent Number: 6,022,351
[45] Date of Patent: Feb. 8, 2000

[54] SKULL CLOSURE DEVICE AND PROCEDURE

[76] Inventors: Paul W. Bremer; Ross L Bremer; Scott Gingold, all of 4550-1 Saint Augustine Rd., Jacksonville, Fla. 32207

[21] Appl. No.: 09/255,334

[22] Filed: Feb. 23, 1999

[51] Int. Cl.⁷ ................................................... A61B 17/56
[52] U.S. Cl. ............................................................. 606/72
[58] Field of Search .................................. 606/61, 65, 69, 606/72, 73

[56] References Cited

U.S. PATENT DOCUMENTS 5,800,436  9/1998  Lerch .

OTHER PUBLICATIONS

"Craniofix" brochure, by Aesculap, 1000 Gateway Blvd. So., San Francisco, CA 94080, 1998.
"Bioplate Biomesh" brochure, Bioplate, Inc., Los Angeles, CA, 1996.

Primary Examiner—Michael Buiz
Assistant Examiner—Daphna Shui
Attorney, Agent, or Firm—Nixon & Vanderhye P.C.

[57] ABSTRACT

A fastener system for use in reattaching a skull flap in an opening formed in a patient's skull during brain surgery, is simple, quick, and easy to use, and is cost effective. The system includes a fastener element and a substantially disc shaped lock element. Both are made of bio-compatible radiolucent rigid plastic material. The fastener element has a substantially disc shaped head and a shank, the shank having substantially flat first and second substantially parallel surfaces having ratchet teeth on them. The shank typically has a thickness, with ratchet teeth, where it extends through a gap between the skull flap and the skull, of about 1–2 mm. The lock element has a through extending opening defined at least in part by locking teeth which cooperate with the ratchet teeth to allow the lock element to be brought tightly into contact with the skull and skull flap to hold the fastener and lock elements in place and to position the skull flap in the skull. The system, once installed, cannot be removed without actually cutting away the components.

20 Claims, 3 Drawing Sheets

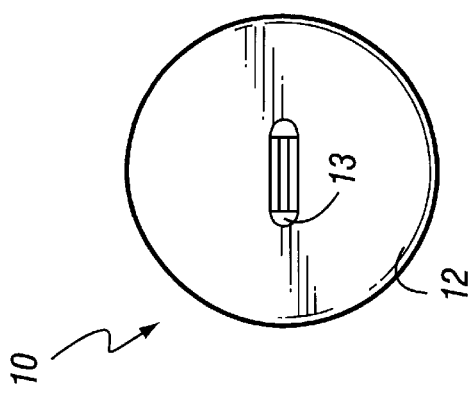
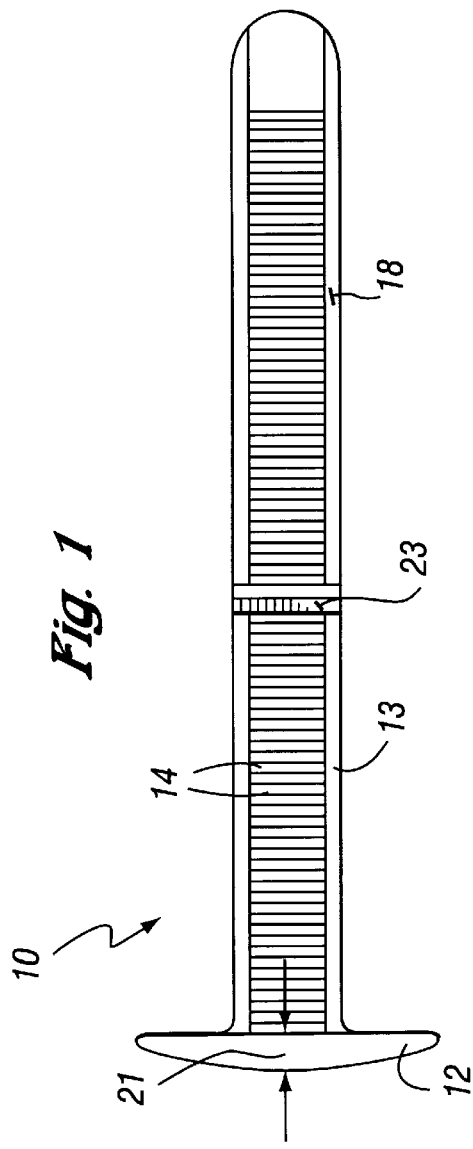
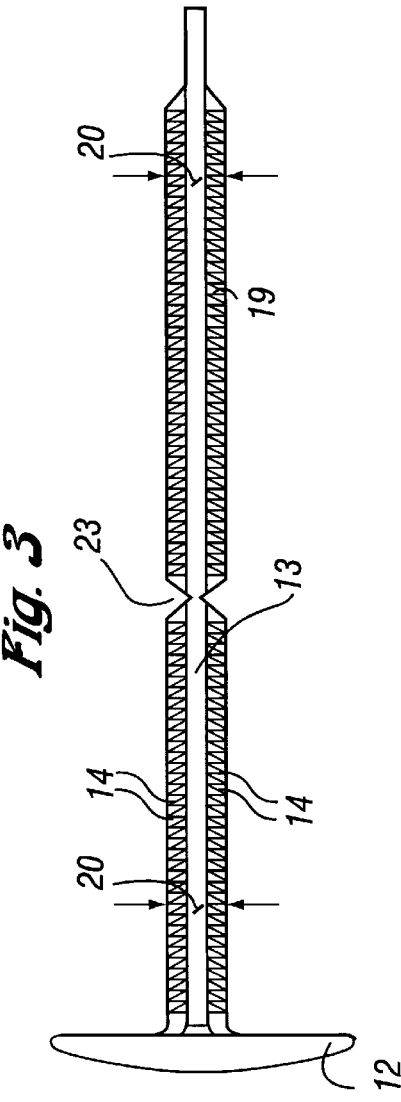

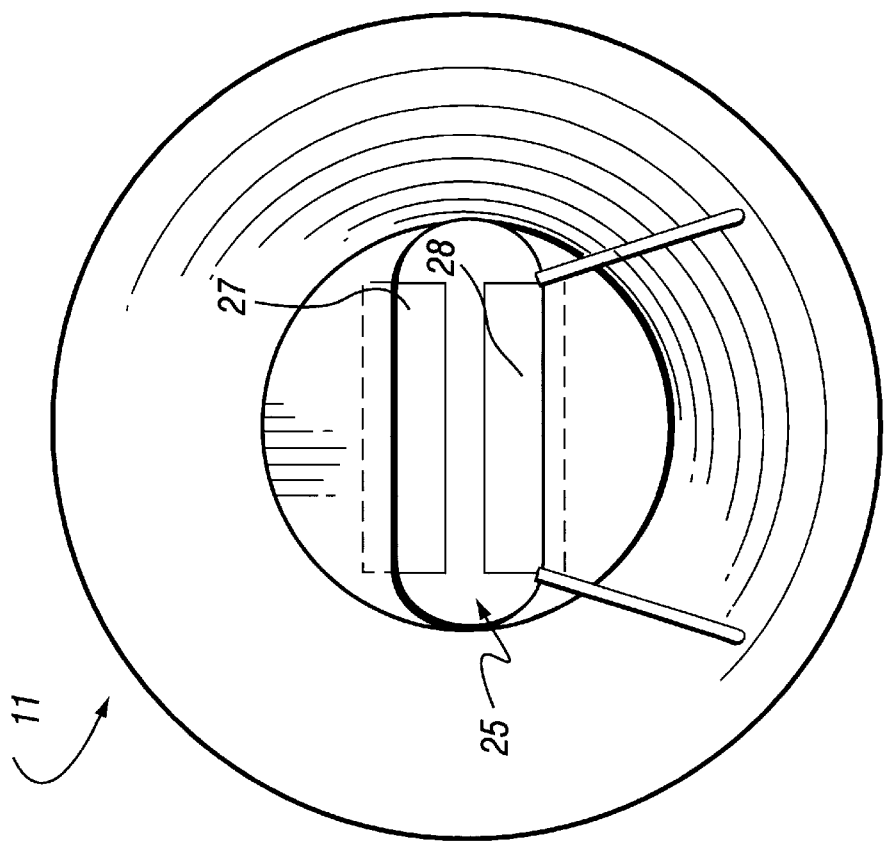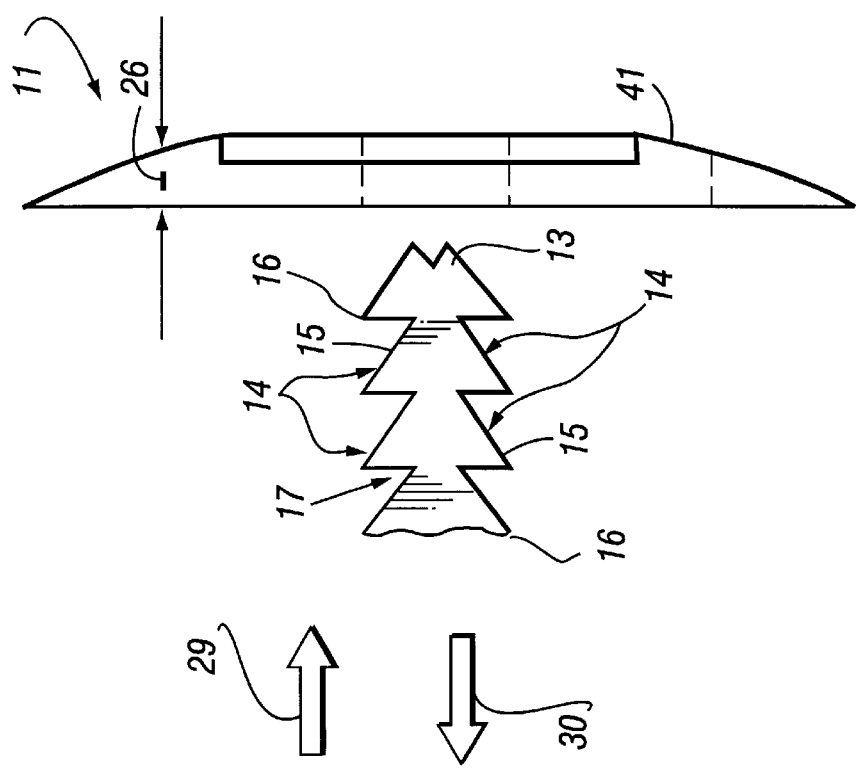

SKULL CLOSURE DEVICE AND PROCEDURE

BACKGROUND AND SUMMARY OF THE INVENTION

The invention relates to a fastening system, particularly for use in reattaching a skull flap, removed during brain surgery, and leaving an opening in a patient's skull, within the skull opening, and a method of reattaching the skull flap using the fastening system.

When most brain surgery is performed, it is necessary to remove a piece of skull to provide access to the brain. This is done with a hand-held, gas powered surgical tool similar to a small router. After a small hole is made in which the bit of the router is placed, the bit is then guided to cut out the piece of the skull required. The blade cuts a gap of about 1.5 mm to 2 mm wide so that the piece removed does not fit back into its hole exactly. The piece that is removed is referred to as a skull "flap".

When the brain surgery is completed, this skull flap must be reattached to the skull. There are several methods of doing this. Most commonly, a series of matching small holes is drilled in the edge of the skull and the edge of the flap. Sutures are then passed through the corresponding holes and the flap is secured back into the skull opening from which it was taken. Because the fit is not exact due to the material removed by the router, the flap always sits slightly below the surface of the skull resulting in a depressed area that is obvious through the skin.

Another common method substitutes stainless steel wire for the suture material and fewer holes are used. There is still the cosmetically objectionable depressed area resulting.

More recently, surgeons have begun to use the titanium micro plates and screws that were developed for internal fixation of facial and finger bones. While this method results in a more cosmetic result, it is extremely expensive.

All of these methods take thirty minutes to one hour of additional surgery after four to six hours of brain surgery.

There is another, newer method just beginning to be marketed in which a titanium rivet is placed inside the skull with the stem of the rivet passing between the skull and the flap. A large "pop rivet" type tool is used to force a titanium button down over the stem of the rivet, locking the flap and the skull in place between them. Three or four of these rivets and buttons are used to secure the flap in place. This method if faster than any of the other methods and less expensive than the titanium plates, but more expensive than sutures or wires.

A major disadvantage of all of the methods that use metal as a material is that the metal components create large artifacts in the CT scans and plain radiographs that are used for post surgical follow up and diagnosis.

In the early 1970's a company by the name of Codman & Shurtleff developed and marketed a similar "rivet and button" system made of soft silicone plastic. This was never a commercial success and was soon withdrawn from the market. Silicone is too soft and flexible to provide sure fixation and the buttons on the outside of the skull were so large that they made very unsightly bumps under the skin.

According to the present invention a fastening system for, and a method of, reattaching a skull flap in a skull opening, are provided which have the major advantages of the above discussed prior art systems, but without the disadvantages. The fixation provided utilizing the fastening system, and practicing the method, of the invention is at least as secure as suturing, the components of the system are radiolucent (that is they will not substantially artifact during CT scans or radiographs), it is faster than the conventional methods, it is little more expensive than suturing or wire, cosmetic results are substantially at least as good as when microplates are used, and the fastening system is easily removable if additional surgery is required. All the components of the fastening system according to the invention are preferably injection molded, and of a biologically compatible plastic that is strong enough so that only three or four of the fastener elements are needed to secure the skull flap in place, and the components are dimensioned and constructed so that they avoid potential injury to the dura mater covering the brain, and do not form unsightly bumps under the skin.

According to one aspect of the present invention a fastening system is provided comprising the following components: A fastener element of bio-compatible radiolucent plastic material comprising a substantially disc shaped head and a shank. The shank having substantially flat first and second substantially parallel surfaces, the surfaces having ratchet teeth thereon. And a substantially disc shaped lock element of bio-compatible radiolucent rigid plastic material having a through extending opening and locking teeth defining at least part of the opening, the locking teeth cooperating with the ratchet teeth to allow the shank to pass through the opening so that the head and lock element can be forced toward each other, but not allowing movement away from each other. The fastening system typically further comprises at least one weakened section of the shank at which the shank breaks off, rather than the ratchet or locking teeth, if the fastening system is overtightened. Typically, the shank, with ratchet teeth, has an operative thickness (that is at least where it extends through the gap between the skull flap and the rest of the skull during reattachment) of about 1–2 mm. The head typically has a thickness of less than about 3 mm and the lock element has a thickness of less than about 2 mm, while the shank has a length of at least about 3 cm. Where the weakened section is at least about 2 cm from the head, the shank typically has a length of at least about 2 cm past the weakened section.

While it may not be necessary for the ratchet teeth to cover all, or even a majority of, the shank, for ease of construction and to accommodate a number of different circumstances, preferably the ratchet teeth cover at least approximately the majority of the length of each surface of the shank, at least up to the weakened section. While a wide variety of plastics may be utilized, a typical plastic that is suitable is acetel plastic, such as duPont's acetal resin sold under the tradename Delrin 100, typically with a Rockwell hardness of about M94, R120 (ASTM method D785, IS02039) (or ±1–4%), and a flex yield strength (ASTM D790) of 99 (or ±1–4%).

According to another aspect of the present invention a fastening system is provided comprising: A fastener element of bio-compatible radiolucent rigid plastic material comprising a substantially disc shaped head and a shank. The shank having a plurality of ratchet teeth thereon, and a thickness of about 1–2 mm. And a substantially disc shaped lock element of bio-compatible radiolucent plastic material having a through extending opening into at least one locking tooth defining at least part of the opening, the at least one locking tooth cooperating with the ratchet teeth to allow the shank to pass through the opening so that the head and lock element can be forced toward each other, but not allowing movement away from each other. The details of the components may be as described above.

According to another aspect of the present invention a method of reattaching a skull flap, removed during brain surgery and leaving an opening in a patient's skull, the flap having an area less than the area of the opening but substantially the same shape, and using a fastening system, comprising a fastener element made of bio-compatible radiolucent rigid plastic having a shank with ratchet teeth and a substantially disc shaped lock element with an opening defined at least in part by at least one locking tooth is provided. The method comprises: (a) Placing a plurality of fastener heads, with shanks facing outwardly, in the skull opening. (b) Placing the skull flap in the skull opening so that a gap is provided between the outer periphery of the skull flap and the periphery of the skull opening, and the fastener shanks extend through the gap. (c) Placing the lock elements over the shanks. (d) For each fastener forcing the lock toward the head so that the ratchet teeth and at least one locking tooth move with respect to each other, until the head and lock element are locked together holding the skull flap in a position closing the skull opening. And (e) removing substantially all shank portions extending outwardly from the lock elements. The sequence of the steps may be varied.

Typically (a)–(e) are practiced using either three or four fastener elements and lock elements only, and the fasteners and lock elements are typically substantially the only structures holding the skull flap in the skull opening. When the shanks have a weakened section, during the practice of (d) one or more shanks break at the weakened section, and as a matter of fact the break can be specifically engineered as part of the fastening procedure. Typically the fasteners and lock elements are dimensioned, constructed, and (a)–(e) are practiced, so that the fastening heads do not injure the patient's dura mater, and so that the lock elements do not form unsightly bumps.

It is the primary object of the present invention to provide a simple, yet highly effective, fastening system for, and method of, reattaching a skull flap to a skull covering the opening from which it was removed. This and other objects of the invention will become clear from an inspection of the detailed description of the invention and from the appended claims.

BRIEF DESCRIPTION OF THE DRAWINGS

FIG. 1 is a top plan view of an exemplary fastener element according to the present invention;

FIG. 2 is a front end view of the fastener element of FIG. 1;

FIG. 3 is a side elevational view of the fastener element of FIGS. 1 and 2;

FIG. 4 is a side view of a lock element according to the present invention, with the ratchet teeth of the fastener element illustrated schematically adjacent thereto;

FIG. 5 is a plan view of the lock element of FIG. 4;

DETAILED DESCRIPTION OF THE DRAWINGS

Figure 6:
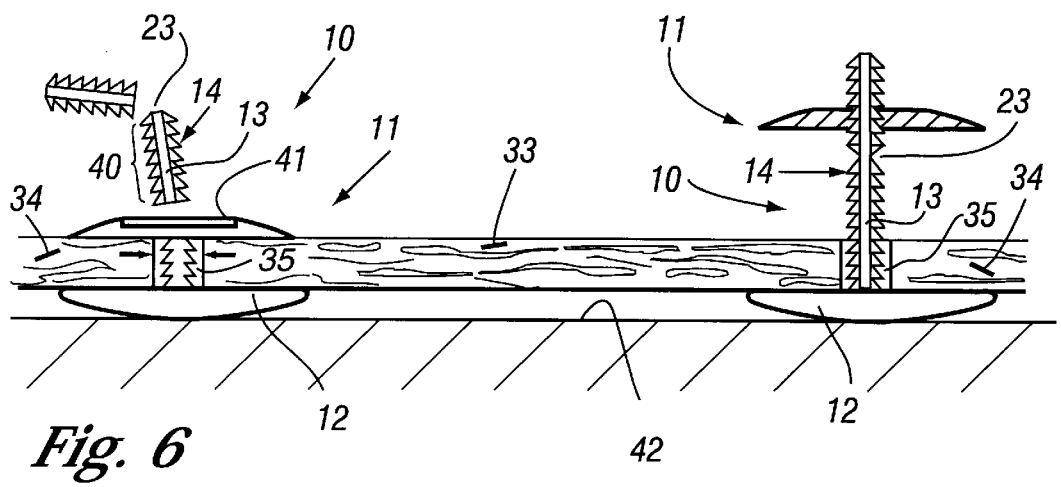
FIG. 6 is a side schematic view showing the use of the fastening system according to the invention in a method of reattaching a skull flap.

A exemplary fastening system according to the invention includes a fastener element shown generally by reference numeral 10 in each of FIGS. 1 through 3, and a lock element shown generally by reference 11. Both of the elements 10, 11 are made of bio-compatible radiolucent rigid plastic material, preferably but not necessarily the same material. An example of suitable material includes acetel plastic, such as duPont's acetel resin sold under the tradename Delrin 100. The material typically has a Rockwell hardness of about M94, R120 (ASTM method D785, IS02039) (or±1–4%), and a flex yield strength (ASTM D790) of 99 (or ±1–4%). While the elements 10, 11 may be made by any suitable technique, they preferably are injection molded.

The fastener element 10 includes a substantially disc shaped head 12, and a shank 13. The shank 13 has a plurality of ratchet teeth 14 associated therewith. Because of the scale the ratchet teeth 14 are not clearly visible in FIGS. 1 through 3, but are shown schematically in enlarged form in FIG. 4, having a construction that is similar to that of a conventional plastic cable tie, with each ratchet tooth having a ramp surface 15 leading up to a point 16 and then a precipitous drop to a valley 17 on the opposite side of the ramp 15 from the point 16. Preferably there is at least one set of ratchet teeth 14, but in the preferred embodiment the shank 13 is flat and thin and has ratchet teeth 14 on opposite substantially flat and substantially parallel surfaces thereof. For example, as seen in FIGS. 1 and 3, the shank 13 may have a substantially flat top surface 18, and is substantially parallel to a corresponding substantially flat bottom surface 19, with a thickness 20 that is small enough so that the shank 13 may readily fit in the gap between a skull flap and skull from which it has been removed. Typically, the dimension 20 is between about 1–2 mm.

The ratchet teeth 14 need only be provided on sufficient portions of the surfaces 18, 19 so as to allow effective fastening of the fastener element 10 in place to hold a skull flap in a skull opening. In the preferred embodiment illustrated, however, ratchet teeth 14 are provided over at least approximately the majority of the surfaces 16, 18.

All of the dimensions of the fastener element 10 are specifically designed to allow its effective use in holding a skull flap in place in a skull opening. For example, the head 12 has a small thickness 21 so that it does not have the potential of injuring the dura mater covering the brain. For example, the dimension 21 is typically less than about 3 mm, e.g. about 2.5 mm. The diameter of the substantially disc shaped head 12 can vary fairly widely, as long as it is greater than about 4 mm, but preferably it is about a centimeter. The shank 13 typically has a length of at least about 3 cm.

In the preferred embodiment illustrated in the drawings, the fastener element 13 has at least one weakened section 23 (e.g. having a thickness significantly less than the thickness 20) at which the shank 13 breaks off, rather than the ratchet teeth breaking, if the fastening system is overtightened. The weakened section 23 may be at least about 2 cm from the head 12, and the shank 13 may have a length of at least about 2 cm past the weakened section 23 (that is on the opposite side thereof from the head 12).

The locking element 11 is a substantially disc shaped element having a through extending opening 25 extending therethrough, and the element 11 is also thin. The element 11 must be thin enough so that it does not form an unsightly bump underneath the skin when it is used to hold the skull flap in place in a skull opening from which it has been removed. For example, the thickness 26 illustrated schematically in FIG. 4 is typically less than about 2 mm. Defining at least part of the opening is at least one locking tooth 27, and preferably a pair (or more) of locking teeth 27, 28, one locking tooth 27, 28 (or set of locking teeth) being provided associated with each set of ratchet teeth 14 on the surfaces 18, 19. The teeth 27, 28 are designed so that they will flex just enough so that when they are engaged by a ramp face 15 of the ratchet tooth 14, they will move out of the way, but it will snap back into place once the point 16 of that tooth 14 has moved therepast, that is the locking tooth 27, 28 falling into the valley 17 between the ratchet tooth 14 and the next tooth 14. However, the teeth 27, 28 will not allow movement in the opposite direction. That is there may be relative movement between the disc shaped locking element 11 and shank 13 not in the direction 29 illustrated in FIG. 4, but not in the direction 30. Once the lock element 11 has been locked into place it can only be removed by destruction thereof.

FIG. 6 illustrates schematically the use of the fastening system according to the invention, comprising the elements 10, 11, to fasten a skull flap 32 into place within an opening in a skull 34 from which it has been removed. As seen in both FIGS. 6 and 7, the skull flap 33 is formed by forming gap 35 in the skull 34 which is typically about 1.5–2 mm wide, as indicated by the dimension 36 in FIG. 7. The thickness 20 of the shank 13, at least adjacent the head 12 where the shank 13 fits in the gap 35, is slightly less than the dimension 36. The method is practiced by placing a plurality of the fastener heads 12, with the shanks 13 facing outwardly as illustrated in FIG. 6, in the opening in the skull 34 from which the skull flap 33 was originally removed. The skull flap 33 has the same basic shape as the opening, just slightly smaller in dimension, so as to provide the gap 35. The skull flap 33 is placed in the opening so that the gap 35 is provided between the outer periphery 37 of the skull flap 33, and the periphery 38 of the skull opening. The fastener shanks 13 extend through the gap 35.

Figure 7:
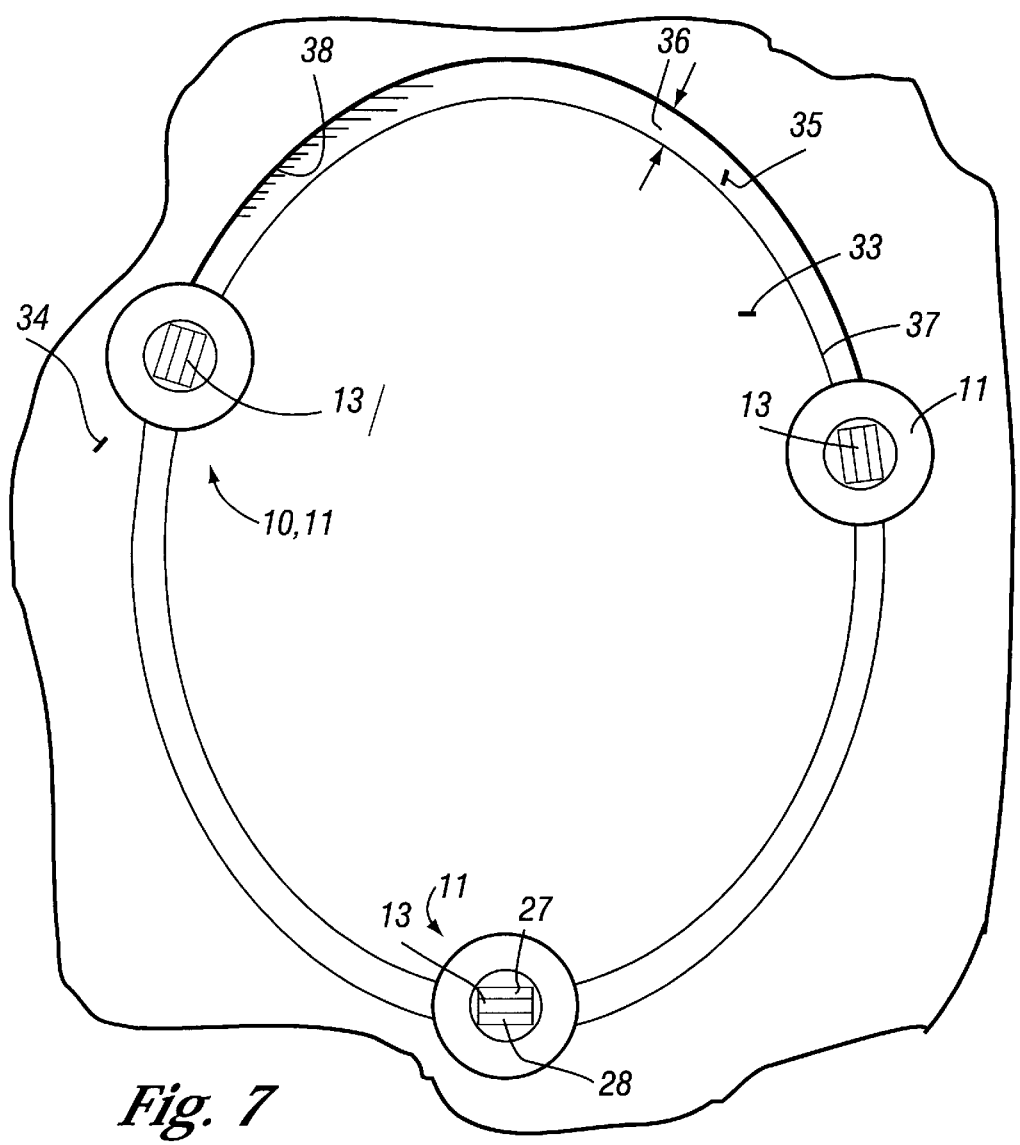
FIG. 7 is a top plan view of the skull flap reattached with three fasteners according to the invention.

The lock elements 11 are placed over the shanks 13, and then for each of the fasteners 10 the lock element 11 is forced toward the head 12 so that the ratchet teeth 14 and the locking teeth 27, 28 move with respect to each other until the head 12 and lock element 11 are locked together holding the skull flap 33 in a position closing the skull opening, as seen for the left side elements 10, 11 in FIG. 6, and as shown for all of the elements in FIG. 7. A forcing action may be provided in any suitable way, but preferably is accomplished using a tool that is substantially the same as a conventional pop rivet tool which holds the shank 13 steady while it pushes the lock element 11 toward the head 12, only modified to accommodate the dimensions and the particular shape and construction of the element 11 and the shank 13.

Finally, substantially all shank 13 portions extending outwardly from the lock elements 11 are removed. In the preferred method, utilizing the preferred shanks 13 according to the invention, the tool that is used to force the lock element 11 toward the head 12 will cause the shank 13 to be stressed so that it breaks at the weakened portion 23, as schematically illustrated in the left side of FIG. 6, indicating that the fastener has been properly tightened. The remaining portion of the shank 13 that extends away from the lock element 11, as illustrated at 40 in FIG. 6, is then removed by cutting it off, with a blade, a heating unit, or in any other suitable conventional manner, so that the outer face 41 of the disc shaped lock element 11 is substantially flush. Then the skin/scalp is placed back over the elements 11.

FIG. 7 schematically illustrates three fastener systems, each comprising an element 10 and an element 11, according to the present invention properly holding the skull flap 33 in place in the skull opening having the interior periphery 38. In the preferred embodiment according to the invention only three or four element sets 10, 11 (three being shown in FIG. 7) are necessary in order to effectively hold the skull flap 33 in place, and preferably the three or four fastening systems defined by the elements 10, 11 are substantially the only structures holding the skull flap 13 properly in place. Also, because of the particular dimensions and construction of the components, the heads 12 do not injure the dura mater 42 (see FIG. 6), and the discs 11 do not provide unsightly bumps when the skin is placed over them. Also, because the elements 10, 11 are radiolucent, they do not significantly artifact when the patient has a CT scan or a plain radiograph.

While it will thus be seen that according to the present invention a very simple, yet effective and cost effective, fastening system for, and method of, reattaching a skull flap in a skull opening after brain surgery have been provided. The fixation provided for the skull flap 33 is at least a secure suturing, all of the components are radiolucent, the method is easier and faster in practice than conventional prior art procedures, the elements 10, 11 are only slightly more expensive than suturing or wiring, the cosmetic results obtained are at least as good as for microplates, and the elements 10, 11 may be easily removed, simply by cutting them away utilizing conventional cutting implements, if additional surgery is required.

While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent systems and methods.

What is claimed is:

1. A fastening system comprising:

a fastener element of bio-compatible radiolucent plastic material comprising a substantially disc shaped head and a shank;

said shank having substantially flat first and second substantially parallel surfaces, said surfaces having ratchet teeth thereon; and a substantially disc shaped lock element of bio-compatible radiolucent rigid plastic material having a through extending opening and locking teeth defining at least part of said opening, said locking teeth cooperating with said ratchet teeth to allow said shank to pass through said opening so that said head and lock element can be forced toward each other, but not allowing movement away from each other.

2. A fastening system as recited in claim 1 further comprising at least one weakened section of said shank at which said shank breaks off, rather than said ratchet or locking teeth, if said fastening system is overtightened.

3. A fastening system as recited in claim 2 wherein said shank, with ratchet teeth, has an operative thickness of about 1–2 mm.

4. A fastening system as recited in claim 3 wherein said head has a thickness of less than about 3 mm and said lock element has a thickness of less than about 2 mm.

5. A fastening system as recited in claim 1 wherein said ratchet teeth cover approximately the majority of the length of each surface of said shank.

6. A fastening system as recited in claim 1 wherein said shank has a length of at least about 3 cm.

7. A fastening system as recited in claim 6 further comprising at least one weakened section of said shank at which said shank breaks off, rather than said ratchet or locking teeth if said fastening system is overtightened.

8. A fastening system as recited in claim 7 wherein said weakened section is at least about 2 cm from said head, and said shank has a length of at least about 2 cm past said weakened section.

9. A fastening system as recited in claim 1 wherein said shank, with ratchet teeth, has an operative thickness of about 1–2 mm.

10. A fastening system as recited in claim 1 wherein said head has a thickness of less than about 3 mm and said lock element has a thickness of less than about 2 mm.

11. A fastening system as recited in claim 1 wherein said plastic is the same for said fastener and lock element, and comprises acetel having a Rockwell hardness of about M94, R120, ±4%.

12. A method of reattaching a skull flap, removed during brain surgery and leaving an opening in a patient's skull, the flap having an area less than the area of the opening but substantially the same shape, and using a fastening system, comprising a fastener element made of bio-compatible radiolucent rigid plastic having a shank with ratchet teeth and a substantially disc shaped lock element with an opening defined at least in part by at least one locking tooth; said method comprising:

(a) placing a plurality of fastener heads, with shanks facing outwardly, in the skull opening;

(b) placing the skull flap in the skull opening so that a gap is provided between the outer periphery of the skull flap and the periphery of the skull opening, and the fastener shanks extend through the gap;

(c) placing the lock elements over the shanks;

(d) for each fastener forcing the lock toward the head so that the ratchet teeth and at least one locking tooth move with respect to each other, until the head and lock element are locked together holding the skull flap in a position closing the skull opening; and (e) removing substantially all shank portions extending outwardly from the lock elements.

13. A method as recited in claim 12 wherein (a)–(e) are practiced using only either three or four fastener elements and lock elements.

14. A method as recited in claim 12 wherein the shanks have a weakened section, and wherein during the practice of (d) one or more shanks break at the weakened section.

15. A method as recited in claim 12 wherein the fasteners and lock elements are dimensioned and constructed, and (a)–(e) are practiced, so that the fastener heads do not injure the patient's dura mater, and so that the lock elements do not form unsightly bumps under the patient's skin.

16. A method as recited in claim 12 wherein (a)–(e) are practiced so that the fasteners and locks are substantially the only structures holding the skull flap in the skull opening.

17. A method as recited in claim 16 wherein (a)–(e) are practiced using only either three or four fastener elements and lock elements.

18. A fastener system comprising:

a fastener element of bio-compatible radiolucent rigid plastic material comprising a substantially disc shaped head and a shank;

said shank having a plurality of ratchet teeth thereon, and a thickness of about 1–2 mm; and a substantially disc shaped lock of bio-compatible radiolucent plastic material having a through extending opening into at least one locking tooth defining at least part of said opening, said at least one locking tooth cooperating with said ratchet teeth to allow said shank to pass through said opening so that said head and lock can be forced toward each other, but not allowing movement away from each other.

19. A fastening system as recited in claim 18 further comprising at least one weakened section of said shank at which said shank breaks off, rather than said ratchet or locking teeth, if said fastening system is overtightened.

20. A fastener system as recited in claim 18 wherein said head has a thickness of less than about 3 mm and said lock element has a thickness of less than about 2 mm and said shank has a length of at least 3 cm; and wherein said plastic is the same for said fasteners and said lock, and comprises acetel having a Rockwell hardness of about M94, R120, ±4%.

* * * * *